United States Patent
Hayashi et al.

(10) Patent No.: US 7,521,463 B2
(45) Date of Patent: Apr. 21, 2009

(54) IMMUNOMODULATORY COMPOUNDS

(75) Inventors: Jun Hayashi, Ellicott City, MD (US); Alexander Mackerell, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 286 days.

(21) Appl. No.: 10/333,605

(22) PCT Filed: Jul. 31, 2001

(86) PCT No.: PCT/US01/41467

§ 371 (c)(1),
(2), (4) Date: Jan. 22, 2003

(87) PCT Pub. No.: WO02/10191

PCT Pub. Date: Feb. 7, 2002

(65) Prior Publication Data

US 2004/0044034 A1    Mar. 4, 2004

Related U.S. Application Data

(60) Provisional application No. 60/221,687, filed on Jul. 31, 2000.

(51) Int. Cl.
| | | |
|---|---|---|
| *A01N 37/02* | (2006.01) | |
| *A01N 57/10* | (2006.01) | |
| *A61K 31/19* | (2006.01) | |
| *A61K 31/22* | (2006.01) | |
| *A61K 31/44* | (2006.01) | |
| *A61K 31/225* | (2006.01) | |

(52) U.S. Cl. ........................ 514/345; 514/546; 514/547; 514/568

(58) Field of Classification Search ................. 514/345, 514/546, 568, 547, 685
See application file for complete search history.

(56) References Cited

U.S. PATENT DOCUMENTS

| 5,281,620 A | 1/1994 | Denny et al. |
| 5,958,935 A | 9/1999 | Davis et al. |
| 6,291,442 B1 * | 9/2001 | Yellen .................... 514/155 |

FOREIGN PATENT DOCUMENTS

WO    WO 99/38845 A1 *    8/1999

OTHER PUBLICATIONS

"Principles of Cancer Therapy". Cecil's Textbook of Medicine (Twenty-First Edition, vol. 1). W.B. Saunders Company, 2000. pp. 1060-1074.*
"Autoimmune Disorders". The Merck Manual of Diagnosis and Therapy (Sixteenth Edition). Merck & Co., Inc. 1992. pp. 339-342.*
Osol A [Editor]. "Chapter 27: Structure-Activity Relationship and Drug Design". Remington's Pharmaceutical Sciences (Sixteenth Edition). Mack Publishing, 1980. pp. 420-435.*
Maybridge Product Code #BTB11478 [Online], Nov. 2007. [Retrieved Nov. 20, 2007]. Retrieved from the Internet: <URL:http://www.maybridge.com>.*
Maybridge Product Code #SPB01890 [Online], Nov. 2007. [Retrieved Nov. 20, 2007]. Retrieved from the Internet: <URL:http://www.maybridge.com>.*
CAS Registry No. 85-54-1. STN Registry File. Retrieved from STN Registry Jul. 1, 2008. One page.*

* cited by examiner

*Primary Examiner*—Ardin Marschel
*Assistant Examiner*—Leslie A Royds
(74) *Attorney, Agent, or Firm*—Millen, White, Zelano, Branigan, P.C.

(57) ABSTRACT

Compounds are described which modulate the tzrosine kinase activity of p56$^{lck}$ and signal transduction pathways in which this enzyme is involved. The invention also relates to compounds which have immunomodulatory activity, e.g., which have immunosuppressant or immunostimulatory activity, and/or which have an antineoplastic effect. The invention further relates to compositions comprising these compounds, and methods of using them. Compounds are described which modulate the tyrosine kinase activity of p56.

23 Claims, No Drawings

IMMUNOMODULATORY COMPOUNDS

This application is filed under 35 U.S.C. 371 based on international application PCT/US01/41467, filed Jul. 31, 2001, and claims benefit of U.S. Provisional Application Ser. No. 60/221,687, filed Jul. 31, 2000, the disclosures of which are incorporated herein by reference in their entirety.

FIELD OF THE INVENTION

This invention relates, e.g., to compounds which modulate the tyrosine kinase activity of $p56^{lck}$ and signal transduction pathways in which this enzyme is involved. The invention also relates to compounds which have immunomodulatory activity, e.g., which have immunosuppressant or immunostimulatory activity, and/or which have an antineoplastic effect. The invention further relates to compositions comprising these compounds, and methods of using them.

DESCRIPTION OF THE INVENTION

In one embodiment, the invention relates to a method of achieving an immunomodulatory effect in a patient in need thereof, comprising administering an effective amount of a compound of the formula

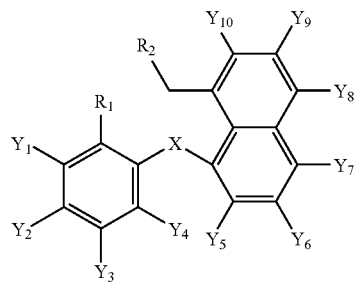

I wherein

X is sulfur, $SO_2$, SO, methylene, oxygen, carbonyl, ethylene, amide, ester or thioester, $R_1$ is a negative charge functional group, $R_2$ is an electronegative group, which can be an amine, amide, urea, carbamide, carbonate, anhydride, thioamide, thiourea, thiocarbamide, thiocarbonate, thioanhydride, hydroxyl, or an ester, e.g., an alkyl ester, acyl ester, aryl ester, alkyl thioester, acyl thioester or aryl thioester, $Y_1$, $Y_2$, $Y_3$, $Y_4$, $Y_5$, $Y_6$, $Y_7$, $Y_8$, $Y_9$, and $Y_{10}$ are, independently, hydrogen, methyl, ethyl, propyl, isopropyl or halogen, and optionally, one or more of the phenyl aromatic rings are replaced by a fused aromatic ring, heteroaromatic ring, or fused heteromatic ring, for example, by replacing 1-3 carbon atoms of one of more of the aromatic rings with N atoms. (Examples include naphthyl, pyridinyl, quinolinyl and isoquinolinyl rings), or of the formula

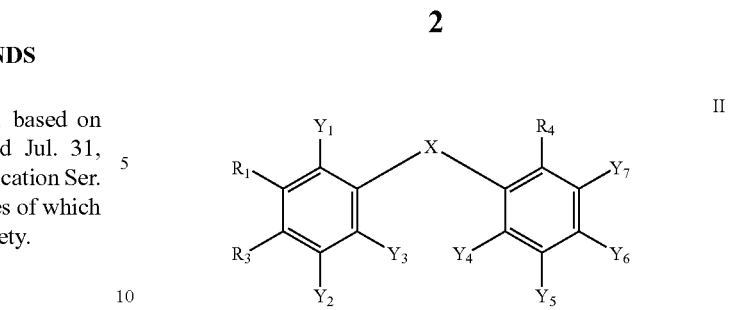

II wherein

X and $Y_1$ to $Y_7$ are as defined above, $R_1$ and $R_4$ are the same or different, and are as defined above for $R_1$, $R_3$ is hydrogen, halogen hydroxyl, amine, methyl, ethyl, propyl or isopropyl, and optionally, one or more of the phenyl aromatic rings are replaced by a fused aromatic ring, heteroaromatic ring, or fused heteromatic ring, for example, by replacing 1-3 carbon atoms of one of more of the aromatic rings with N atoms. (Examples include naphthyl, pyridinyl, quinolinyl and isoquinolinyl rings), or of the formula

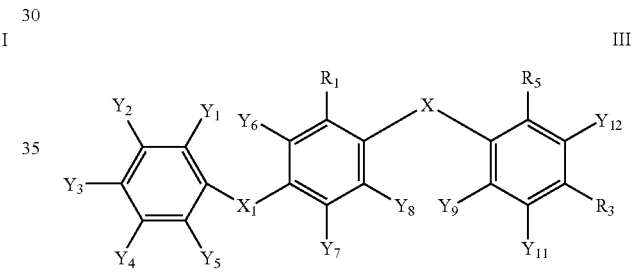

III wherein

X and $R_1$ are as defined above, and $Y_1$ to $Y_{12}$ are as defined above for $Y_1$ to $Y_{10}$, $X_1$ is a sulfur, $SO_2$, SO, methylene, oxygen, carbonyl, ester, thioester or amide, $R_3$ and $R_5$ are the same or different, and are as defined above for $R_3$, and optionally, one or more of the phenyl aromatic rings are replaced by a fused aromatic ring, heteroaromatic ring, or fused heteromatic ring, for example, by replacing 1-3 carbon atoms of one of more of the aromatic rings with N atoms. (Examples include naphthyl, pyridinyl, quinolinyl and isoquinolinyl rings), or a pharmaceutically acceptable salt thereof.

Preferably, the negative charge functional group of the compounds above is a —COOH, amide, ester, nitro, phosphate or sulfate radical (by phosphate is meant esters of phosphorous based acids, such as phosphorous or phosphoric acid; by sulfate is meant esters of sulfur-based acids, such as sulfonic or sulfinic acid); the hydrogen bond acceptor is preferably a carboxylic acid or an ester of carboxylic acid, e.g., an alkyl ester, acyl ester, aryl ester, alkyl thioester, acyl thioester or aryl thioester.

In a most preferred embodiment, the compound is

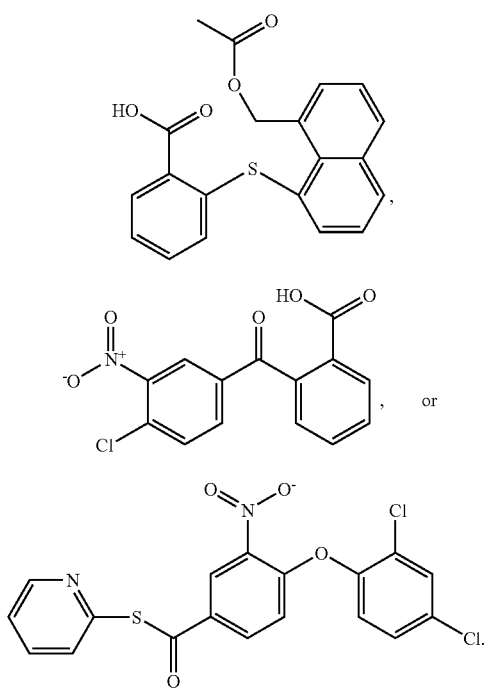

In exemplary embodiments, $X_1$ and X are, independently, O, S, thioester or carbonyl, $R_1$ (and independently $R_4$) is COOH or nitro, $R_2$ is an alkyl ester, amino or OH, $R_3$ (and independently $R_5$) is H, Cl, F, OH or methyl, the Y's are independently H, methyl, F or Cl, and the "phenyl" rings remain phenyl rings or are naphthyl or pyridinyl.

In another embodiment, the invention relates to a method for achieving an antineoplastic effect in a patient in need thereof, comprising administering an effective amount of a compound of formulas I, II or III as noted above.

In another embodiment, the invention relates to a method of modulating the binding of a $p56^{lck}$ molecule via an SH2 domain thereof to a corresponding cellular binding protein, and/or modulating the activity of a $p56^{lck}$ molecule via binding to an SH2 domain thereof, comprising binding to an SH2 domain of said $p56^{lck}$ molecule to a compound of formulas I, II or III, and more preferably, compounds of formulas I', II' or III', as noted above.

In another embodiment, the invention relates to a method for achieving an antineoplastic effect in a patient in need thereof, comprising administering an effective amount of a compound of formulas I', II', or III'.

In another embodiment, the invention relates to a method of inhibiting hyperproliferative cell growth in a patient in need thereof, comprising administering an effective amount of a compound of formulas I, II, III, I', II', or III'.

In another embodiment, the invention relates to a method of achieving an immunomodulatory effect in a patient in need thereof, comprising administering an effective amount of a compound of formulas I', II', or III'.

The compound of formula I' above (compound I') has a molecular weight of about 352 and the chemical formula, $C_{20}H_{16}O_4S$. It activates $p56^{lck}$ kinase activity and results in stimulation and activation of T-cells. Compound I' can be used, e.g., as an immunostimulant.

The compound of formula II' above (compound II') has a molecular weight of about 305 and the chemical formula, $C_{14}H_8O_5ClN$. It activates $p56^{lck}$ kinase activity at low concentrations (doses) and inhibits activity at high concentrations (doses). Compound II' can be used, e.g., as an immunostimulant or as an immunosuppressant, or as an antineoplastic agent, depending on the concentration (dosage) of the compound.

The compound of formula III' above (compound III') has a molecular weight of about 421 and the chemical formula, $C_{18}H_{10}Cl_2N_2O_4S$. It inhibits $p56^{lck}$ kinase activity and can be used, e.g., as an immunosuppressant or as an antineoplastic agent.

In a preferred embodiment, a compound of the invention does not comprise a phosphotyrosine or related moiety.

All compounds can be prepared fully conventionally, using known reaction chemistry, starting from known materials or materials conventionally preparable. [See, e.g., Houben-Weyl, Methoden der Organischen Chemie [Methods of Organic Chemistry], Georg-Thieme-Verlag, Stuttgart]. For example, a compound of the invention can be synthesized via a $SN_{AR}$ reaction of the species,

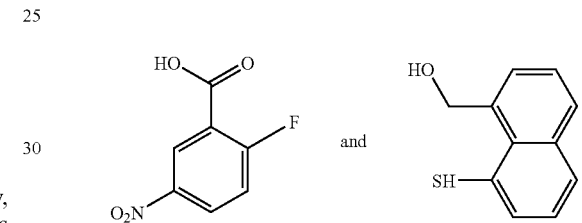

Many compounds of the invention are readily available from standard sources, such as chemical supply houses, or can be generated from commercially available compounds by routine modifications such as those described above. For example, compounds I, II and III noted above can be obtained from the Maybridge Chemical Company, LTD (Maybriege PLC; Trevillet, Tintagel; Cornwall, PL34 OHW; England). Compound I' is Maybridge #BTB11478; compound II' is Maybridge #SB00529; and compound III' is Maybridge #SPB01890.

Among the advantages of the compounds of the invention are that the molecules are not susceptible to enzymatic hydrolysis (as are certain peptide and protein modulators of protein tyrosine kinase activity), and that they exhibit good cell permeability characteristics.

Without wishing to be bound to any particular mechanism, this invention relates, e.g., to compounds that interact specifically with proteins, e.g., protein tyrosine kinases, which are involved in intracellular signaling pathways, in particular to compounds that interact with SH2 domains of such tyrosine kinases, and more particularly to compounds that interact with an SH2 domain of the $p56^{lck}$ src family tyrosine kinase. Among other functions, the $p56^{lck}$ protein is involved in signal transduction pathways involved in T cell antigen receptor activation signaling required for mounting an active immune response, and in aspects of cell proliferation, e.g., proliferation of neoplastic cells. It is proposed that compounds of the invention, by interacting with $p56^{lck}$, particularly with an SH2 domain thereof, modulate the kinase activity of the protein and/or modulate its ability to interact with a corresponding cellular binding protein, and thereby modulate immune responses, directly or indirectly, and neoplastic cell proliferation. Compounds of the invention can either enhance or inhibit signal transduction pathways, including downstream signal transduction processes in a signal transduction pathway, or they can be biphasic, either enhancing or inhibiting, depending on conditions. The effect of any given compound can be routinely determined by screening in one or more of the assays described herein or other fully conventional assays.

The non-catalytic domains of p56$^{lck}$ kinase, e.g. the SH2 domain(s), mediate specific intramolecular and intermolecular interactions that are important for the regulation of p56$^{lck}$ function; they exert both negative and positive effects on kinase activity. In general, the intramolecular interaction keeps p56$^{lck}$ in an inactive state, and the intermolecular interactions facilitate p56$^{lck}$ kinase action. For example, the SH2 domain can positively regulate p56$^{lck}$ enzymatic activity by targeting p56$^{lck}$ to specific cellular sites [ITAM (immunoreceptor trosine based activation motifs) phosphotyrosines] where substrate phosphorylation is needed; and p56$^{lck}$ that is bound to phosphtyrosine sites via its SH2 domain can exhibit higher enzymatic activity, thereby enhancing further phosphorylation of substrates. Without wishing to be bound to any particular mechanism as to how this is accomplished, it is proposed that the compounds which bind to the SH2 domain can either increase (activate, enhance, stimulate), decrease (suppress, inhibit, depress), or have no effect on, kinase activity and attendant cellular phosphorylation events (e.g., processes involved in intracellular signaling).

p56$^{lck}$ plays an important role in modulating immune responses. p56$^{lck}$ is a T-cell specific kinase, the majority of which is associated with CD4 (in $T_H$ cells) and CD8 (in cytotoxic T cells). The p56$^{lck}$ kinase is responsible, e.g., for an early step in activating T cells—the phosphorylation of ITAM in CD3 chains—which in turn initiates multiple intracellular cascades of biochemical events leading to, e.g., actin polymerization, enhanced gene transcription, cellular proliferation and differentiation. p56$^{lck}$ also plays an important role in a second important step in the activation of T cells—immunological synapse formation. The compounds of the invention can modulate the immune response by, e.g. modulating T-cell activation, or indirectly by modulating downstream processes of a signal transduction pathway. As used in this application, the term "modulate" means to change, e.g., to increase (activate, enhance, stimulate) or decrease (suppress, inhibit, depress) a reaction or an activity. Compounds of the invention can be said to modulate the binding of a p56$^{lck}$ SH2 domain to a "corresponding cellular binding protein," which term, as used herein, refers to any cellular binding protein whose binding to p56$^{lck}$ is mediated by SH2 domains. Such corresponding cellular binding proteins include, e.g., CD3 chains, ZAP-70, p62, Lad, CD45, Sam68 or the like.

Many protein tyrosine kinases play a role in regulating cellular events, including gene activation and/or regulation, and thus, e.g., in cell proliferation. p56$^{lck}$ is a proto-oncogene, which has been implicated in a number of pathological conditions that involve undesirable hyperproliferation of cells. For example, overexpression of constitutively active p56$^{lck}$ has been observed in murine and human lymphomas, suggesting that p56$^{lck}$-mediated phosphorylation of cellular proteins stimulates lymphocyte proliferation. In addition, overexpression and activation of p56$^{lck}$ appears to play an important role in the human lymphoid cell transformation induced by Epstein-Barr virus and Herpesvirus Saimiri. Moreover, transgenic mice overexpressing wild type p56$^{lck}$ and a constitutively active form of p56$^{lck}$ in thymocytes develop thymoma, suggesting that even the overexpression of wild type p56$^{lck}$ can transform cells under these conditions. Compounds of the invention, e.g. compounds which inhibit p56$^{lck}$ activity, are useful for the treatment of conditions involving hyperproliferative cell growth, either in vitro (e.g., transformed cells) or in vivo. Conditions which can be treated or prevented by the compounds of the invention include, e.g., a variety of neoplasms, including benign or malignant tumors, a variety of hyperplasias, or the like. Compounds of the invention can achieve the inhibition and/or reversion of undesired hyperproliferative cell growth involved in such conditions.

As used herein, the term "hyperproliferative cell growth" refers to excess cell proliferation. The excess cell proliferation is relative to that occurring with the same type of cell in the general population and/or the same type of cell obtained from a patient at an earlier time. "Hyperproliferative cell disorders" refer to disorders where an excess cell proliferation of one or more subsets of cells in a multicellular organism occurs, resulting in harm (e.g., discomfort or decreased life expectancy) to the multicellular organism. The excess cell proliferation can be determined by reference to the general population and/or by reference to a particular patient (e.g., at an earlier point in the patient's life). Hyperproliferative cell disorders can occur in different types of animals and in humans, and produce different physical manifestations depending upon the affected cells. Hyperproliferative cell disorders include, e.g., cancers, blood vessel proliferative disorders, fibrotic disorders, and autoimmune disorders.

Activities and other properties of the compounds of the invention (and comparisons of those activities to those of art-recognized, comparison compounds) can be measured by any of a variety of conventional procedures.

A variety of in vitro assays can be used to measure biological and/or chemical properties of the compounds, and are conventional in the art. For example, in vitro binding studies can determine the affinity and the specificity of binding of the compounds, e.g., to a p56$^{lck}$ SH2 domain. Example 4 illustrates a method to determine $K_D$ and $IC_{50}$ values, using tritiated compounds and purified, recombinant p56$^{lck}$ SH2 domains. Similar assays can show that compounds bind selectively in vitro to a particular site, e.g., to the p56$^{lck}$ SH2 domain, but not to other sites, e.g., Hck, Fyn, Src, Shc or ZAP-70 SH2 domains. Example 5 illustrates an in vitro co-immunoprecipitation (IP) kinase assay. Again, similar assays can show the specificity of binding of the compounds. Example 6 illustrates an assay to determine specificity of the binding.

Other conventional in vitro assays can measure the effect (e.g., inhibition or enhancement) of the compounds on biological activities associated with tyrosine protein kinases, e.g., p56$^{lck}$. p56$^{lck}$ activities which are involved in immune responses include, e.g., the phosphorylation of, e.g., tyrosine in the ITAM consensus sequence present in certain molecules, e.g., CD3 chains; immunological synapse formation, e.g., with corresponding cellular binding proteins; or the like. Example 1 illustrates an in vitro assay for Jurkat cell-activation-dependent phosphorylation, an activity that is correlated with T-cell activation. Compound I' is shown to stimulate the phosphorylation, and compounds II' (at high dosage) and III' to be inhibitory. The effects are shown to be dose-dependent. Example 2 illustrates an in vitro assay for cell viability, which indicates if a compound is cytotoxic or cytostatic. Compound III' is shown to exhibit a reversible inhibition of Jurkat cell growth. Example 3 illustrates an in vitro assay for IL-2 production, an activity which is correlated with T-cell activation. Compound III' is shown to inhibit IL-2 production in OKT-3 treated Jurkat cells. Example 7 illustrates a mixed lymphocyte culture assay.

A variety of in vivo assays can be used to demonstrate immunomodulatory properties of the compounds. Such in vivo assays, and appropriate animal models for disease conditions that can be treated with the compounds, are well-known to those of skill in the art. For example, animal models for rheumatoid arthritis are illustrated in Example 8.

Assays to measure the effect of compounds (e.g., phosphotyrosine kinase inhibitors) on cell growth proliferation) and cell transformation are conventional. A variety of typical assays are described, e.g., in Kelloff, G. J., et al., Cancer Epidemiol Biomarkers Prev., 1996. 5(8), p. 657-66; Wakeling, A. E., et al., Breast Cancer Res Treat, 1996, 38(1), 67-73; Yano, S., et al., Clin Cancer Res, 2000, 6(3), p. 957-65; Reedy, K. B., et al., Cancer Res, 1992, 52(13), p. 3636-41; Peterson, G. and S. Barnes, Prostate, 1993; 22(4), p. 335-45; Scholar, E. M. and M. L. Toews, Cancer Lett, 1994, 87(2); 159-62; Spinozzi, F., et al., Leuk Res, 1994, 18(6), p. 431-9; Kondapaka, B. S. and K. B. Reddy, Mol Cell Endoctinol, 1996, 117(1), p. 53-8; Moasser, M. M., et al., Cancer Res, 1999, 59(24), p. 6145-52; Li, Y., M. Bhuivan & F. H. Sarkar, Int J Oncol, 1999, 15(3), p. 525-33; Baguley, B. C., et al. Eur J Cancer, 1998, 34(7), p. 1086-90; and Bhatia, R., H. A. Munthe, and C. M. Verfaillie, Leukemia, 1998, 12(11), p. 1708-17.

Variations of the assays described herein, as well as other conventional assays, are well known in the art. Such assays can, of course, be adapted to a high throughput format, using conventional procedures.

Moreover, conventional methods of computer-aided rational drug design can provide an indication as to whether an inventive compound has the proper "fit" to, and is complementary to, a region of the protein which is important for specificity of binding, e.g., a $p56^{lck}$ SH2 domain, as opposed to, e.g., Hck, Fyn, Src, Shc or ZAP-70 SH2 domains. In particular, such methods can indicate whether a compound is complementary to the pY+3 binding site of $p56^{lck}$. The terms "specific binding" or "specificity of binding" as used herein mean that an inventive compound interacts with, or forms or undergoes a physical association with, a particular SH2 domain (e.g., a $p56^{lck}$ SH2 domain) with a higher affinity, e.g., a higher degree of selectivity, than for other protein moieties (e.g., SH2 domains of other protein kinases). Furthermore, properties of the compounds, such as, e.g., solubility, chemical stability and the absence of chemical groups known to impart toxicity, can be analyzed on the basis of known properties of certain chemical substituents, which are well known to those of skill in the art. See, e.g., Opera, J. Comput.-Aided Mol. Des., 2000. 14: p. 251-264.

The compounds of the invention are effective for binding to, e.g., $p56^{lck}$ SH2 domains, and for modulating the activity of, e.g., $p56^{lck}$ in animals, e.g., mammals, such as mouse, rat, rabbit, pets, (e.g., mammals, birds, reptiles, fish, amphibians), domestic (e.g., farm) animals, and primates, especially humans. The inventive compounds exhibit, e.g., immunomodulatory activity and/or antineoplastic activity, and are effective in treating diseases in which, e.g., aberrant regulation or activity of tyrosine kinase (e.g., $p56^{lck}$) and/or intracellular signaling responses are involved. For example, compounds which stimulate immune responses (immunostimulants) are useful for treating or preventing naturally occurring immunosuppression or immunosuppression from a variety of conditions and diseases. Compounds which depress immune responses (immunosuppressants) are useful for treating or preventing, e.g., autoimmune diseases which are characterized by inflammatory phenomena and destruction of tissues caused by the production, by the immune system, of the body's own antibodies, or for suppressing rejection during, eg., tissue or organ transplantation.

Compounds which inhibit cell proliferation are useful for treating conditions characterized by cell hyperproliferation, e.g., as antineoplastic agents. Compounds of the invention are also useful as research tools, e.g., to investigate cell signaling.

In accordance with a preferred embodiment, the present invention includes methods of treating patients suffering from depressed immune systems resulting from, e.g., chemotherapy treatment, radiation treatment, radiation sickness, or HIV/AIDs; conditions associated with primary B-cell deficiency (such as, e.g., Bruton's congenital a-γ-globulinemia or common variable immunodeficiency) or primary T-cell deficiency (such as, e.g., the DiGeorge and Nezelof syndromes, ataxia telangiectasia or Wiskott-Aldrich syndrome); severe combined immunodeficiency (SCID), etc.; with an immunostimulant of the invention. The immunostimulants can also be used for vaccines (e.g., anti-bacterial, anti-fungal, anti-viral or anti-protozoiasis), particularly for patients having immunocompromised states; or for anti-neoplastic vaccines.

In another preferred embodiment, the invention includes methods of treating patients suffering from autoimmune disorders, such as, e.g., rheumatoid arthritis, glomerulonephritis, Hashimoto's thyroiditis, multiple sclerosis, T cell leukemia, systemic lupus erythematosus, myasthenia gravis, autoimmune hemolytic anemia, autoimmune thrombocytopenic purpura, type 1 diabetes, Chrohn's disease, Grave's disease, celiac disease, or the like, with an immunosuppressant of the invention. Immunosuppressants of the invention are also useful for treating tissue or organ transplant rejection, e.g., hyper-acute or chronic graft-vs-host disease, allograft or xenograft rejection, etc.

As mentioned, the compounds of the invention also inhibit hyperproliferation of cells, e.g., they can exhibit anti-neoplastic activity. As a result, the inventive compounds are useful in the treatment of a variety of conditions, e.g. cancers involving T cells and B cells. Among the types of cancer which can be treated with compounds of the invention are e.g., leukemias, lymphomas, ovarian cancer and breast cancer.

Compounds of the invention can be attached to an agent that, e.g., targets certain tumors, such as an antibody which is specific for a tumor-specific antigen. In this manner, compounds of the invention can be transported to a target cell in which they then can act. The compounds can be further attached to a conventional cytotoxic agent (such as a toxin or radioactivity). When the inventive molecule binds to its target, e.g., $p56^{lck}$, it not only will inhibit the enzymatic activity, but will also destroy the target, and/or the cell in which the target resides, by means of the toxin.

The preferred aspects include pharmaceutical compositions comprising a compound of this invention and a pharmaceutically acceptable carrier and, optionally, another active agent as discussed below; a method of inhibiting or stimulating a $p56^{lck}$ kinase, e.g., as determined by a conventional assay or one described herein, either in vitro or in vivo (in an animal, e.g., in an animal model, or in a mammal or in a human); a method of modulating an immune response, e.g., enhancing or inhibiting an immune reaction; a method of treating a disease state, e.g., an autoimmune disease, a neoplasm, etc.; a method of treating a disease state modulated by $p56^{lck}$ kinase activity, in a mammal, e.g., a human, including those disease conditions mentioned herein.

The present invention also relates to useful forms of the compounds as disclosed herein, such as pharmaceutically acceptable salts and prodrugs of all the compounds of the present invention. Pharmaceutically acceptable salts include those obtained by reacting the main compound, functioning as a base, with an inorganic or organic acid to form a salt, for example, salts of hydrochloric acid, sulfuric acid, phosphoric acid, methane sulfuric acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and chlorine salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts are prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyannates, tosylates, mesylates and undecanoates.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

The compounds of the invention can be administered alone or as an active ingredient of a formulation. Thus, the present invention also includes pharmaceutical compositions of compounds of formulas I, II or III containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Isol, editor), 1553-1593 (current edition).

In view of their high degree of selective $p56^{lck}$ kinase inhibition or stimulation, the compounds of the present invention can be administered to anyone requiring $p56^{lck}$ kinase inhibition or stimulation. Administration may be accomplished according to patient needs, for example, orally, nasally, parenterally (subcutaneously, intravenously, intramuscularly, intrasternally, and by infusion) by inhalation, rectally, vaginally, topically and by ocular administration. Injection can be, e.g., intramuscular, intraperitoneal, intravenous, etc.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time-release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

The compounds can be administered as the sole active agent or in combination with other pharmaceutical agents, such as other agents which inhibit or stimulate tyrosine kinases, signal transduction processes, cell proliferation and/or immune responses. Inhibitory agents include, e.g., cyclosporine, FK506, rapamycin, leflunomide, butenamindes, corticosteroids, atomeric acid, dipeptide derivative, tyrphostin, Doxorubicin or the like. In such combinations, each active ingredient can be administered either in accordance with its usual dosage range or a dose below its usual dosage range.

The dosages of the compounds of the present invention depend upon a variety of factors including the particular syndrome to be treated, the severity of the symptoms, the age, sex and physical condition of the patient, the route of administration, the frequency of the dosage interval, the particular compound utilized, the efficacy, toxicology profile, pharmacokinetic profile of the compound, and the presence of any deleterious side-effects, among other considerations.

By "effective dose" or "therapeutically effective dose" is meant herein, in reference to the treatment of a cancer, an amount sufficient to bring about one or more of the following results: reduce the size of the cancer; inhibit the metastasis of the cancer; inhibit the growth of the cancer, preferably stop cancer growth; relieve discomfort due to the cancer; and prolong the life of a patient inflicted with the cancer.

A "therapeutically effective amount," in reference to the treatment of a hyper-proliferative cell disorder other than a cancer refers to an amount sufficient to bring about one or more of the following results: inhibit the growth of cells causing the disorder, preferably stopping the cell growth; relieve discomfort due to the disorder; and prolong the life of a patient suffering from the disorder.

A "therapeutically effective amount", in reference to treatment of an autoimmune disorder refers to an amount sufficient to bring about one or more of the following results: inhibit or ameliorate the symptoms of the disease; inhibit progressive degeneration of cells involved in the disorder; relieve discomfort due to the disorder; and prolong the life of a patient suffering from the disorder.

A "therapeutically effective amount", in reference to treatment of a patient undergoing tissue or organ transplantation refers to an amount sufficient to bring about one or more of the following results: inhibit or prevent rejection of the transplanted material; relieve discomfort resulting from rejection of the transplait; and prolong the life of a patient receiving a transplant.

A "therapeutically effective amount," in reference to treatment of an immunosuppressive patient refers to an amount sufficient to bring about one or more of the following results: increase the number of T cells or number of activated T cells; reduce the immuosuppressed state of the patient; relieve discomfort due to the disorder; and prolong the life of a patient suffering from the disorder.

The compounds of the invention are administered at dosage levels and in a manner customary for $p56^{lck}$ kinase inhibitors or stimulators, or other analogous drugs, such as those mentioned above. For example, cyclosporine is administered (for transplants) at about 7.95±2.81 mg/kg/day (see PDR (Physician's Desk Reference)); FK506 is administered (for transplants) at about 0.15-0.30 mg/kg/day (see PDR); and rapamycin is administered (for transplants) at about 2-6 mg/day, e.g., about 0.024 mg/kg/day for an 81 kg adult (see Thomas A. Stargy Transplantation Institute web site). See also, e.g., disclosures in U.S. Pat. Nos. 5,688,824, 5,914,343, 5,217,999, 6,133,301 and publications cited therein.

For example, compounds I and III of the invention can be administered, in single or multiple doses, at a dosage level of, for example, 1 µg/kg to 500 mg/kg of body weight of patient/day, preferably between about 100 µg/kg/day and 25 mg/kg/day. For compound II, dosages are adjusted so as to generate an immunostimulatory or immunosuppressive effect, as desired. A lower dosage (immunostimulatory) can be between about 1 µg/kg/day and 750 µg/kg/day, preferably between about 10 µg/kg/day and 500 mg/kg/day. A higher dosage (immunosuppressive) can be between about 1 mg/kg/day and 750 mg/kg/day, preferably between about 10 mg/kg/day and 450 mg/kg/day.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

In the foregoing and in the following examples, all temperatures are set forth uncorrected in degrees Celsius; and, unless otherwise indicated, all parts and percentages are by weight.

EXAMPLES

Example 1

Jurkat Cell Activation-dependent Phosphorylation

Phosphorylation in Jurkat cells activated by the monoclonal antibody, OKT-3, is correlated with T-cell activation.

A. Compounds are tested for their effect on OKT-3 activated Jurkat cells. OKT-3 is a monoclonal antibody against CD3-ε chain. Treatment of Jurkat cells with OKT-3 antibody for 5 min at 37° C. activates Jurkat cells and induces tyrosine phosphorylation of several cellular proteins. In JCaM1.6 Jurkat cells expressing $p56^{lck}$ with defective kinase activity, the OKT-3-mediated phosphorylation of cellular proteins does not take place, indicating that $p56^{lck}$ plays an essential role in this process. Experiments are carried out to determine if compounds of the invention, or known compounds which can serve as standards, affect cellular tyrosine phosphorylation stimulated by OKT-3 in Jurkat cells. For example, compounds II', and III' are shown to exhibit have inhibitory activity at 100 µM, and compound I' to exhibit stimulatory activity.

The assay is performed as follows: Jurkat cells ($1 \times 10^6$ cells) in RPMI 1640 supplemented with 10% fetal bovine serum (FBS) are treated with OKT-3 antibody (0.2 µg) and compounds (100 µM) for 5 min at 37° C. Cultures are immediately placed on ice after the incubation period, washed 3 times with cold PBS and lysed in 20 µl of SDS-sample buffer. Samples are briefly sonicated and boiled for 5 min and applied to SDS-PAGE (12% gel). After SDS-PAGE, proteins are blotted onto Immobilon P membrane (Millipore) for western blot analysis. Membranes are blocked overnight with 5% dried milk in TBST (Tris buffered saline containing 1% triton X-100). After washing, blots are incubated with monoclonal anti-phosphotyrosine antibody for 1 h in TBST followed by 1 hr incubation with horseradish peroxidase (HRP)-conjugated goat anti-mouse IgG. Blots are developed using enhanced chemiluminescence (ECL, Pierce).

B. Dose response experiments are performed. For example, compound I' is shown to significantly stimulate tyrosine phosphorylation of Jurkat cellular proteins in a dose-dependent manner. Compound II' stimulates tyrosine phosphorylation of cellular proteins at a lower dose (0.1 and 1 µM), but inhibits phosphorylation at the higher dose (100 µM). Compound III' completely inhibits tyrosine phosphorylation of cellular proteins.

The assay is performed as follows: Western blot analyses using anti-phosphotyrosine antibody are performed. Compounds (e.g., inventive compounds I', II' and III') are added at concentrations of 0.1, 1, 10 and 100 µM. Cells are cultured as above. Compound I' is shown to induce dose-dependent stimulation of tyrosine phosphorylation, while Compound III' inhibits tyrosine phosphorylation even at the lowest concentration (0.1 µM tested. Compound II' gives a biphasic response, and stimulates tyrosine phosphorylation at lower doses (0.1 and 1 µM) while inhibiting phosphorylation at a higher dose (100 µM).

Example 2

Effect on Jurkat Cell Viability

Compounds can be tested to determine whether they are cytotoxic or cytostatic. To test whether a compound which inhibits OKT-3-mediated stimulation of tyrosine phosphorylation has a cytotoxic effect on Jukat cells, its effect on the growth of Jurkat cells is tested. For example, compound III' at 10 µM is shown to exhibit some cytostatic effect, inhibiting the growth of Jurkat cells, but no cytotoxic effect is observed. Jurkat cells resume their normal rate of growth 24 hours after the addition of compound III', indicating that the effect of compound III' on growth is reversible.

Example 3

Inhibition of IL-2 Production in Jurkat Cells

Interleukin 2 (IL-2) is an autocrine growth factor for T cells, the production of which requires T cell antigen receptor and co-receptor generated activation signals in normal T cells. The production of IL-2 is a hallmark of T cell activation signaling, leading to the clonal expansion of antigen-specific T cell clones. In Jurkat cells, treatment of cells with OKT-3 leads to the production of IL-2. In order to test whether a compound which inhibits OKT-3 induced tyrosine phosphorylation of cellular proteins also inhibits IL-2 production, Jurkat cells are treated with OKT-3 in the presence or absence of the compound. For example, about 50% inhibition of IL-2 production is observed when cells are treated with 10 µM compound III' at the time of OKT-3 treatment. At lower concentrations, compound III' has no observable effect. Unlike the complete inhibition of OKT-3 induced tyrosine phosphorylation, the inhibition of IL-2 production by compound III' is partial.

The assay is performed as follows: Jurkat cells ($1 \times 10^6$ cells) are treated with OKT-3 antibody (0.2 µg) in the presence or absence of compounds (e.g., Compound III') (0.1, 1 and 10 µM) for 24 h in RPMI 1640+10% FBS. At the end of the incubation period, culture media are harvested and assayed for human IL-2 by RIA. Cells treated with OKT-3 only and PMA+Ionomycin serves as a positive control. Untreated cells serve as a negative control. IL-2 production is not detected in untreated cells. Cells treated with 10 µM of Compound III' are shown to inhibit IL-2 production by 44%. The standard deviation is 0.23 pg/ml.

Example 4

Binding to the SH2 Domain Using [$^3$H]-compound

Purified recombinant P56$^{lck}$-SH2 domain expressed as a GST-fusion protein in bacteria is bound to either anti-GST agarose beads or glutathione-agarose beads. These beads bind the GST-p56$^{lck}$-SH2 protein and facilitate the separation of [$^3$H]-test compound bound SH2 domain from unbound compound. Alternatively, dextran-coated activated charcoal solution is used to separate bound from unbound compounds.

Determination of $K_D$: The binding affinity of a compound is determined by applying standard Scatchard analysis where the binding assay is performed in the presence of a fixed amount of the [$^3$H]-compound and an increasing amount of cold compound. The $K_D$ of the compound is calculated using the Ligand Program (Munson & Rodbard 1980), Analytical Biochem., 107, 220-239. The co-P is evident from, e.g., Sun et al., 1987, Biochem. Biophys. Res. Comm. 148, 603-608.

Determination of $IC_{50}$: In addition to the determination of $K_D$, the $IC_{50}$ value for the compounds to inhibit p56$^{lck}$-SH2 domain binding to the N-terminal pY of CD3 ζITAM2 is measured. The SH2 domain of p56$^{lck}$ has the highest binding affinity (0.1 µM) to the N-terminal pY of the second ITAM of CD3ζ chains. A synthetic peptide corresponding to this region is made and conjugated to agarose beads (ζ-NpY-ITAM2-agarose). P56$^{lck}$ binds to ζ-NpY-ITAM2-agarose through its SH2 domain and can be precipitated. Using the recombinant p56$^{lck}$ GST-SH2 protein, binding assays using ζ-NpY-ITAM2-agarose are carried out in the presence or absence of the compounds at various concentrations (0.01~100 µM) in RIPA buffer. After 2 h of the binding reaction at room temperature, beads are harvested and washed three times with RIPA buffer. The relative amounts of GST-SH2 bound to the ζ-NpY-ITAM2-agarose are measured by a colorimetric assay after incubating the beads with anti-GST antibody and HRP-conjugated secondary antibody and HRP enzyme substrate. The OD read out from the binding of GST-SH2 to the ζ-NpY-ITAM2-agarose in the absence of the compound serves as positive control and represents the 100% bound level. Background (ζ-NpY-ITAM2-agarose without GST-SH2) is subtracted front each value. Assays are carried out in triplicate and the average from three independent assays are used to calculate $IC_{50}$ values for each compound.

Example 5

Co-immunoprecipitation Experiments

The binding of compounds to the p56$^{lck}$ SH domain pY+3 pocket affects the SH2-mediated interaction of p56$^{lck}$ with phosphotyrosine residues of cellular target proteins. For example, the treatment of cells with an inhibitor compound inhibits the association of p56$^{lck}$ with CD3ξ and ZAP-70, whereas an increase in the association occurs following treatment with a stimulator compound. The presence of these molecular interactions is assessed by co-immunoprecipitation assays in activated Jurkat cells in the presence or absence of the compounds. Using this assay (in conjunction with p56$^{lck}$ kinase assays as described elsewhere herein), one can estimate the $IC_{50}$ of a compound for blocking the molecular interactions and the $ED_{50}$ of a compound for activating kinase activity. These values are generally in the vicinity of the $K_D$ of the compound binding to the SH2 domain, provided that the effect of the compound is mediated by binding to the SH2 domain of p56$^{lck}$.

Jurkat cells ($5 \times 10^6$ to $1 \times 10^7$/ml; 1 ml/condition) are activated using OKT-3 antibody (1 µg/$5 \times 10^6$ cells) in the presence or absence of the compound to be tested (0.01 to 100 µm). Following 10 min of activation at 37° C., cells are harvested and lysed using RIPA or NP-40 lysis buffer. After removing insoluble materials, the supernatant is treated with 1 to 2 µg of antibody against either CD3ξ or ZAP-70. Immune complex is precipitated using Protein A or G conjugated agarose beads (10 µl of 50% slur) at 4° C. Beads are harvested and washed three times with lysis buffer, boiled for 2 min., resolved on SDS PAGE (e.g., 12.5%) and blotted on Immobilon-P membrane for Western blot analysis, using anti-p56$^{lck}$ antibody. Samples from non-activated cells and activated cells in the presence of the compound serve as negative and positive controls. Blots are also re-probed with the precipitating antibody to ensure that equal amounts of protein (either CD3ξ or ZAP-70) precipitates from each sample. The presence of co-immunoprecipitating p56$^{lck}$ is examined. A semi-quantitative analysis can also be carried out by altering the compound concentrations in the assay and measuring the relative amount of co-immunoprecipitating p56$^{lck}$. Quantitation is performed by performing EIA (using spectrophotometric assay following HRP-conjugated 2° antibody+chromogenic substrate), chemoluminescence (using image analyzer following HRP-conjugated 2° antibody+ECL) or phosphorimage analysis (using [$^{125}$I]-2° antibody). IC$_{50}$ values for each compound are determined.

Example 6

Demonstration of Specificity of Binding

Based on sequence homology and other considerations five additional SH2 domain containing kinases, including ZAP-70, which contains two pY binding sites, are selected for testing of specificity, both computationally and experimentally. These proteins are listed in Table 1:

TABLE 1

SH2 domains used for determination of selectivity

| SH2 domain | EF loop | FB loop | βG strand | PDB Entry |
|---|---|---|---|---|
| lck | Ser-Pro-Arg | Pro | Arg-Pro-Cys | 1LKK |
| Hck | Ser-Pro-Arg | Ser | Val-Pro-Cys | 1QCF |
| Fyn | Thr-Thr-Arg | Glu | Val-Pro-Cys | 1AOT |
| Src | Thr-Ser-Arg | Ser | Asn-Val-Cys | 1BKL |
| Shc | Lys-Asp | Glu | Gln-Pro-Val | 1TCE |
| ZAP-70, N[a] | Ala-Gly-Gly | Cys | Lys-Pro-Cys | NA[b] |
| ZAP-70, C[a] | Pro-Glu-Gly | Asp | Glu-Ala-Cys | NA[b] |

[a]ZAP-70 contains 2 phosphotyrosine binding sites in the N and C-terminal regions, designated ZAP-70, N and ZAP-70, C, respectively
[b]NA: Not available from the PDB, however, the structure was obtained by the authors.

Specificity is determined via differential binding of the SH2 domains in Table 1 with the phosphopeptides listed in Table 2. The SH2 domains are selected based on homology with P56$^{lck}$ as well as the availability of 3D structal data. Phosphopeptides are selected based on their SH2 domain specificity. The ζ-ITAM-2-C and ζ-ITAM-1 peptides are specific for p56$^{lck}$ and ZAP-70, respectively. All Src kinases including p56$^{lck}$ and Shc are known to bind with similar affinity to the hamster polyoma middle T antigen peptide that contains the pYEEI sequence.

FITC-labeled streptavidin or by scintillation counter using [$^{125}$I]-labeled streptavidin. OD (or cpm) reading of ζ-ITAM2-C peptide without compound constitutes 100% bound. OD (or cpm) reading of SH2 only constitutes the blank. IC$_{50}$ values for each compound are determined. Alternatively, the assay is adapted to use glutathione-agarose beads to separate SH2 domain after the incubation period. K$_D$ for each compound is determined using binding competition assay.

Example 7

Mixed Lymphocyte Culture Assay

Another readout assay that is used to measure biological response is a mixed lymphocyte culture assay in which lymphocytes from two different strains of mice with different histocompatibility antigens are mixed. Due to the difference in the histocompatibility antigens, resting T cells from both strains of mice undergo blast transformation and propagate. As in any T cell activation process, the activation of p56$^{lck}$ is essential. Therefore, the modulation of p56$^{lck}$ activity can be quantified as the downstream modulation in the levels of [$^3$H]-TDR incorporation into DNA.

Lymph node or splenic lymphocytes are harvested from two different allogeneic strains of mice. Cells (1×10$^6$) from each strain are mixed in 96 well cultureplates containing 200 μl of culture medium in the presence or absence of the compound (0.1~100 μM) and cultured for 72 h. Six hours before harvest, 0.5 μCi of [$^3$H]-TdR is added to each well. At the end of the culture period, cells are harvested on a glass fiber filter using a cell harvester. Filters are washed with PBS and then with ethanol and [$^3$H]-TdR incorporated into DNA is measured using scintillation counting. Experiments are carried out in triplicate. Cells cultured in the absence of the compound serve as a positive control. Cells from each strain of mouse cultured in the absence of allogeneic lymphocytes serve as the negative control. The compounds are added every

TABLE 2

Phosphopeptides used in the selectivity binding experiments

| | pY Peptide | SH2 domain |
|---|---|---|
| SEQ ID No. 1 | TATEGQpYQPQP (ζ-ITAM-2-C) | p56$^{lck}$ |
| SEQ ID No. 2 | GQNQLpYNELNLGRREEpYDVLDKR (ζ-ITAM-1) | ZAP-70 |
| SEQ ID No. 3 | EQpYEEIPIA (hamster polyoma middle T) | p56$^{lck}$, Src, Hck, Shc, Fyn |

A solid phase binding competition assay between the compounds and the phosphopeptides is used. SH2 domains are PCR amplified and expressed as GST-fusion proteins in *E. coli*. The GST-fusion protein is purfied on a glutathione column. SH2 domains are cleaved off using thrombin and purified on a gel filtration column. Synthetic phosphotyrosine containing peptides listed in Table 2 are synthesized using conventional methods. These peptides are biotinylated at the N-terminus, away from the SH2 docking site, using kits available from Pierce (Rockford, Ill.). A 96-well EIA plate is coated with a purified SH2 domain (1 μg/well; ~100 nmol). Biotinylated peptide (~200 nmol) in the presence or absence of varying concentrations (pmol to μmol) of compound is added. Biotinylated peptide bound to the SH2 domain is then measured in various ways, such as by colorimetric assay using HRP-streptavidin+substrate, by fluorescence using 12 h. The compounds that inhibit protein phosphorylation and IL-2 production have a similar effect on [$^3$H]-TdR incorporation.

Example 8

Inhibition in vivo of Immune Response of Delayed-Type Hypersensitivity (DTH) and Anti-type II Collagen-induced Rheumatoid Arthritis in Mice One experimental model is DTH response to PPD. DTH reaction is a typical T cell immune response and, thus well suited to be used for assessing the in vivo effect of the compounds. Mice are immunized using BCG in complete Freund's adjuvant (CFA). After the initial immunization, a tuberculin skin test is performed. Bilateral regions of BCG immunized mouse skin are treated with hair removal cream.

Interdermal injection of tuberculin is administered in two hair-removed sites. The compound dissolved in DMSO is applied to one of the sites every 12 h. The other site is treated with DMSO only and serves as an internal positive control. After one week, diameters of DTH reactions for both control and treated sites are measured. Five mice are used in a group. Statistical analysis is carried out to determine effective dose required for 50% reduction in the DTH skin test over control. Treatment is carried out with animals anesthetized (using vaporizer, 2% isoflurane). Animals are kept under anesthesia till DMSO is completely absorbed to the skin. The amount of DMSO applied to each site is kept minimal (~10 µl).

In addition to the DTH reaction, experiments are performed using collagen-induced arthritis (CIA) in mice. CIA is an experimental model for rheumatoid arthritis (RA) in human. A commercial kit is available to reliably induce CIA in mice in a short period of time. Monoclonal antibody cocktail against type II collagen is injected into mice, i.v. RA develops within 24-48 h after injection of the antibody cocktail and exacerbated swelling of the two hind paws becomes evident by day 6. One of the paws from each aal is treated with the compound dissolved in DMSO. The other paw is treated with DMSO only and serves as an internal positive control. Swelling of the paws is measured. Thickness of the paws from saline injected, DMSO-treated control mice serves as negative control. Hind paws are dipped in DMSO solution (with or without the compound to be tested) for 10 seconds twice daily at 12 h intervals. Animals are kept under anesthesia till DMSO is completely absorbed. Five mice are used in a group. Statistical analysis is carried out to determine the effective dose required for 50% reduction in the swelling of paws over the control for the inhibitory compounds. Treatment is carried out using mice under anesthesia.

From the foregoing description, one skilled in the art can easily ascertain the essential characteristics of this invention, and without departing from the spirit and scope thereof, can make changes and modifications of the invention to adapt it to various usage and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above and in the figures are hereby incorporated in their entirety by reference.

What is claimed is:

1. A method of modulating the binding of a p56$^{lck}$ molecule via an SH2 domain thereof to a cellular binding protein selected from the group consisting of CD3 chains, ZAP-70, p62, Lad, CD45, and Sam68, or modulating the activity of a p56$^{lck}$ molecule via an SH2 domain thereof, wherein said method achieves the treatment of a disorder treated by immunostimulation and comprises administering to a patient in need thereof an effective amount of a compound of formula

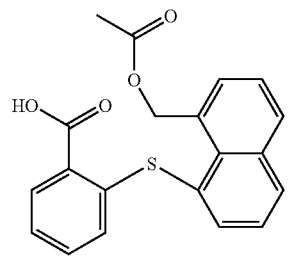

or a pharmaceutically acceptable salt thereof, and binding to an SH2 domain of said p56$^{lck}$ molecule by the compound of formula I' or the pharmaceutically acceptable salt thereof.

2. A method of modulating the binding of a p56$^{lck}$ molecule via an SH2 domain thereof to a cellular binding protein selected from the group consisting of CD3 chains, ZAP-70, p62, Lad, CD45, and Sam68, or modulating the activity of a p56$^{lck}$ molecule via an SH2 domain thereof, wherein said method achieves the treatment of a disorder treated by immunosuppression, and comprises administering to a patient in need thereof an effective amount of a compound of formula

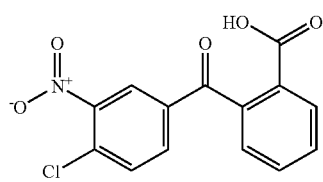

or a pharmaceutically acceptable salt thereof, and binding to an SH2 domain of said p56$^{lck}$ molecule by the compound of formula II' or the pharmaceutically acceptable salt thereof.

3. A method of claim 2, which achieves the treatment of a hyperproliferative cell disorder other than cancer by administering the compound of formula II' in an effective amount to a patient in need thereof.

4. A method of claim 2, which achieves the treatment of an autoimmune disorder by administering the compound of formula II' in an effective amount to a patient in need thereof.

5. A method of claim 2, which achieves the treatment of a tissue or organ rejection in a patient undergoing tissue or organ transplantation by administering the compound of formula II' in an effective amount to a patient in need thereof.

6. A method according to claim 2, which achieves the treatment of rheumatoid arthritis, glomerulonephritis, Hashimoto's thyroiditis, systemic lupus erythematosus, multiple sclerosis, T cell leukemia, myasthenia gravis, autoimmune hemolytic anemia, autoimmune thrombocytopenic purpura, type 1 diabetes, Chrohns disease, Graves disease, celiac disease, hyper acute or chronic graft-vs-host disease, or an allograft or xenograft rejection by administering in an effective amount the compound of formula II' to a patient in need thereof of treatment of rheumatoid arthritis, glomerulonephritis, Hashimoto's thyroiditis, systemic lupus erythematosus, multiple sclerosis, T cell leukemia, myasthenia gravis, autoimmune hemolytic anemia, autoimmune thrombocytopenic purpura, type 1 diabetes, Chrohns disease, Graves disease, celiac disease, hyper acute or chronic graft-vs-host disease, or an allograft or xenograft rejection.

7. A method of modulating the binding of a p56$^{lck}$ molecule via an SH2 domain thereof to a cellular binding protein selected from the group consisting of CD3 chains, ZAP-70, p62, Lad, CD45, and Sam68, or modulating the activity of a p56$^{lck}$ molecule via an SH2 domain thereof,
wherein said method achieves the treatment of a disorder treated by immunosuppression, and comprises administering to a patient in need thereof an effective amount of a compound of formula

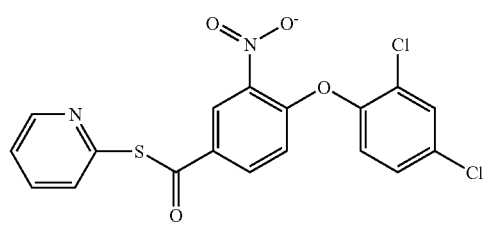

III' or a pharmaceutically acceptable salt thereof, and binding to an SH2 domain of said p56$^{lck}$ molecule by the compound of formula III' or the pharmaceutically acceptable salt thereof.

8. A method of claim 7, which achieves the treatment of a hyperproliferative cell disorder other than cancer by administering the compound of formula III' in an effective amount to a patient in need of treatment of a hyperproliferative cell disorder other than cancer.

9. A method of claim 7, which achieves the treatment of an autoimmune disorder by administering the compound of formula III' in an effective amount to a patient in need of treatment of an autoimmune disorder.

10. A method of claim 7, which achieves the treatment of a tissue or organ rejection in the patient undergoing tissue or organ transplantation by administering a compound of formula III' in an effective amount to a patient in need of treatment of a tissue or organ rejection.

11. A method according to claim 7, which achieves the treatment of rheumatoid arthritis by administering the compound of formula III' in an effective amount to a patient in need of treatment of rheumatoid arthritis.

12. A method according to claim 7, which achieves the treatment of rheumatoid arthritis, glomerulonephritis, Hashimoto's thyroiditis, systemic lupus erythematosus, multiple sclerosis, T cell leukemia, myasthenia gravis, autoimmune hemolytic anemia, autoimmune thrombocytopenic purpura, type 1 diabetes, Chrohns disease, Graves disease, celiac disease, hyper acute or chronic graft-vs-host disease, or an allograft or xenograft rejection by administering in an effective amount the compound of formula III' to a patient in need thereof of treatment of rheumatoid arthritis, glomerulonephritis, Hashimoto's thyroiditis, systemic lupus erythematosus, multiple sclerosis, T cell leukemia, myasthenia gravis, autoimmune hemolytic anemia, autoimmune thrombocytopenic purpura, type 1 diabetes, Chrohns disease, Graves disease, celiac disease, hyper acute or chronic graft-vs-host disease, or an allograft or xenograft rejection.

13. A method of treating rheumatoid arthritis, glomerulonephritis, Hashimoto's thyroiditis, systemic lupus erythematosus, multiple sclerosis, T cell leukemia, myasthenia gravis, autoimmune hemolytic anemia, autoimmune thrombocytopenic purpura, type 1 diabetes, Chrohns disease, Graves disease, celiac disease, hyper acute or chronic graft-vs-host disease, or an allograft or xenograft rejection, comprising administering to a patient in need thereof the compound of formula

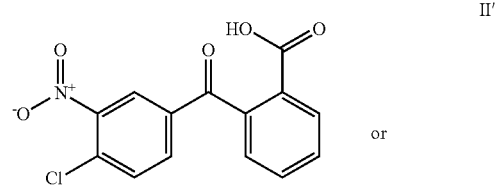

II' or

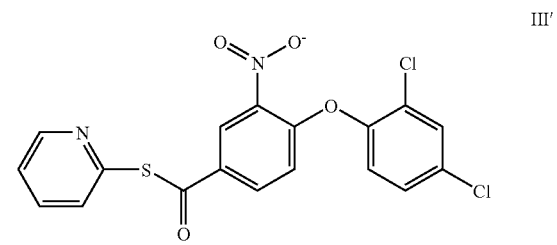

III' or a pharmaceutically acceptable salt thereof.

14. A method according to claim 13, which achieves the treatment of glomerulonephritis, Hashimoto's thyroiditis, or systemic lupus erythematosus by administering the compound of formula II' or III' in an effective amount to a patient in need of treatment of glomerulonephritis, Hashimoto's thyroiditis, or systemic lupus erythematosus.

15. A method according to claim 13, which achieves the treatment of multiple sclerosis by administering the compound of formula II' or III' in an effective amount to a patient in need of treatment of multiple sclerosis.

16. A method according to claim 13, which achieves the treatment of T cell leukemia by administering the compound of formula II' or III' in an effective amount to a patient in need of treatment of T cell leukemia.

17. A method according to claim 13, which achieves the treatment of myasthenia gravis by administering the compound of formula II' or III' in an effective amount to a patient in need of treatment of myasthenia gravis.

18. A method according to claim 13, which achieves the treatment of autoimmune hemolytic anemia, or autoimmune thrombocytopenic purpura by administering the compound of formula II' or III' in an effective amount to a patient in need of treatment of autoimmune hemolytic anemia, or autoimmune thrombocytopenic purpura.

19. A method according to claim 13, which achieves the treatment of type 1 diabetes by administering the compound of formula II' or III' in an effective amount to a patient in need of treatment of type 1 diabetes.

20. A method according to claim 13, which achieves the treatment of Chrohns disease, or Graves disease by administering the compound of formula II' or III' in an effective amount to a patient in need of treatment of Chrohns disease, or Graves disease.

21. A method according to claim 13, which achieves the treatment of celiac disease by administering the compound of formula II' or III' in an effective amount to a patient in need of treatment of celiac disease.

22. A method according to claim 13, which achieves the treatment of hyper acute or chronic graft-vs-host disease, or an allograft or xenograft rejection by administering the compound of formula II' or III' in an effective amount to a patient in need of treatment of hyper acute or chronic graft-vs-host disease, or an allograft or xenograft rejection.

23. A method of treating an immunosuppressive disorder, comprising administering to a patient in need thereof the compound of formula

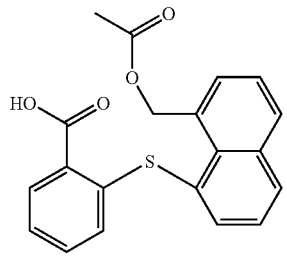

I' or a pharmaceutically acceptable salt thereof.

* * * * *